(12) United States Patent
Wu

(10) Patent No.: US 9,226,870 B2
(45) Date of Patent: Jan. 5, 2016

(54) PORTABLE ELECTRONIC APPARATUS HAVING VISION CARE FUNCTIONS

(71) Applicant: Jung-Tai Wu, Kaohsiung (TW)

(72) Inventor: Jung-Tai Wu, Kaohsiung (TW)

( * ) Notice: Subject to any disclaimer, the term of this patent is extended or adjusted under 35 U.S.C. 154(b) by 0 days.

(21) Appl. No.: 14/293,167

(22) Filed: Jun. 2, 2014

(65) Prior Publication Data

US 2015/0103311 A1    Apr. 16, 2015

(30) Foreign Application Priority Data

Oct. 11, 2013 (CN) .......................... 2013 1 0473269

(51) Int. Cl.
*A61B 3/10* (2006.01)
*A61H 5/00* (2006.01)
*A61B 3/00* (2006.01)
*A61B 3/02* (2006.01)

(52) U.S. Cl.
CPC *A61H 5/00* (2013.01); *A61B 3/005* (2013.01); *A61B 3/02* (2013.01); *A61H 2201/0153* (2013.01); *A61H 2201/50* (2013.01); *A61H 2201/5043* (2013.01)

(58) Field of Classification Search
USPC .......................................... 351/203, 218, 246
See application file for complete search history.

(56) References Cited

U.S. PATENT DOCUMENTS

| 4,408,846 | A | 10/1983 | Balliet |
| 5,528,323 | A * | 6/1996 | Fujieda et al. ................ 351/218 |
| 7,393,102 | B2 | 7/2008 | Horie |

FOREIGN PATENT DOCUMENTS

| CN | 2060068 | U | 8/1990 |
| CN | 2289545 | Y | 9/1998 |
| CN | 2313572 | Y | 4/1999 |
| CN | 2770617 | Y | 4/2006 |
| CN | 201759836 | U | 3/2011 |
| CN | 203089800 | U | 7/2013 |
| TW | M460651 | U | 9/2013 |

* cited by examiner

*Primary Examiner* — Hung Dang
(74) *Attorney, Agent, or Firm* — Rabin & Berdo, P.C.

(57) ABSTRACT

A portable electronic apparatus has a portable electronic device, a lens assembly, a control unit and a display module. The portable electronic device has a shell with a chamber and an opening communicating with the chamber. The lens assembly is mounted in the opening of the shell. The display module is mounted in the chamber of the shell. The control unit is mounted in the portable electronic device to control the display module to project various object images into a user's eyes. The user can exercise the eyes by releasing the eye muscles, tightening the eye muscles, rolling the eyes upwards, downwards, leftwards, rightwards, or rolling the eyes circularly when the user looks at the projected object images. Vision defects, such as myopia and astigmatism, can be relieved.

8 Claims, 10 Drawing Sheets

PORTABLE ELECTRONIC APPARATUS HAVING VISION CARE FUNCTIONS

CROSS-REFERENCE TO RELATED APPLICATIONS

This application claims the benefit of China patent application No. 201310473269.7, filed on Oct. 11, 2013, the disclosure of which is incorporated herein in its entirety by reference.

BACKGROUND OF THE INVENTION

1. Field of the Invention

The present invention relates to a portable electronic apparatus, and more particularly to a portable electronic apparatus having vision care functions.

2. Description of Related Art

There are multiple eye muscles attached to a person's eyes. The eye muscles are like rubber bands. In order to maintain elasticity, the eye muscles should be regularly trained, such as being repeatedly released and tightened. However, if the eye muscles stay at a tightened or a released status for a long time, the eye muscles will gradually lose their elasticity and affect the vision of the eyes.

For example, the ciliary muscles are tightened for clearly observing an object close to the eyes and are released for observing an object far from the eyes. If the ciliary muscles lose the elasticity, the ciliary muscles cannot be properly tightened or released for viewing objects at various distances, and this will cause hyperopia or myopia. As a result, a person with hyperopia fails to observe an object close to the eye, and a person with myopia fails to observe an object far from the eyes.

For vision care, the eye muscles should be exercised to keep the elasticity. The user can look at a near object for a while for tightening the ciliary muscles and afterwards look into the distance for releasing the ciliary muscles. Hence, the ciliary muscles can be trained, and the eye muscles can thus keep the elasticity to maintain the vision. In addition, the user can exercise the extraocular muscles of each eye by circularly rolling the eyes. The eye exercises can excite the optic nerves of the eyes to promote the sense of equilibrium in the brain. In addition, doing the eye exercises can smooth the corneas of the eyes to relieve astigmatism.

Various vision caring devices have been invented. For example, the vision caring devices disclosed in China patent No. CN2060068U, CN2289545Y and CN2313572Y, and U.S. Pat. No. 7,393,102 and U.S. Pat. No. 4,408,846 are constructed by mechanical components, such as wheels, shafts and bulbs, such that these conventional vision caring devices are heavy and not portable. It is inconvenient for a user to carry these vision caring devices by hands. The conventional vision caring devices have to be put on a desk, and the user has to come close to the desk to use them. With such low portability, the user cannot use the conventional vision caring devices anywhere.

China patent No. CN2770617Y includes two separate LED (light emitting diode) strings and two electrodes used to be electrically connected to a user's acupoints. Each of the LED strings has multiple LEDs. The LEDs in the LED strings are alternately and sequentially activated to form light spots moving close toward the eyes or far away from the eyes. The electrodes are used to excite the user's acupoints by electronic signals. China patent No. CN201759836U includes two separate LED strings and two air bags. Each of the LED strings has multiple LEDs. The LEDs in the LED strings are alternately and sequentially activated to form light spots moving close toward the eyes or far away from the eyes. The air bags can be filled with air and expanded to massage the eyes' acupoints. However, the light spots in CN2770617Y and CN201759836U can only move forwards and backwards. The user can only train the ciliary muscles without training the extraocular muscles. The eye muscles are thus not thoroughly exercised.

SUMMARY OF THE INVENTION

An objective of the present invention is to provide a portable electronic apparatus having vision care functions. The present invention is portable, such that the user can carry the present invention by hands and use it anywhere.

The portable electronic apparatus of the present invention has a portable electronic device, a lens assembly, a control unit and a display module. The portable electronic device has a shell with a chamber and an opening communicating with the chamber. The chamber is shielded from exterior light. The lens assembly is mounted in the opening of the shell. The control unit is mounted in the portable electronic device. The display module is mounted in the chamber of the portable electronic device and is at a position opposite to the lens assembly. The display module is controlled by the control unit. The display module is selected from a single light source, a screen of a display, and a group of light sources mounted on a carrier.

Under the condition that the display module is mounted in parallel with the lens assembly, the object image projected from the lens assembly can be a light spot moving forwards (close toward the user's eye), moving backwards (away from the user's eye), upwards, downwards, leftwards, rightwards, or moving circularly in a clockwise direction or a counter-clockwise direction. When the display module is a screen of a display, the display can show a dynamic image to motivate the user for vision care exercises.

In another embodiment, when the display module is mounted obliquely relative to the lens assembly, the object image projected from the lens assembly can be a light spot moving forwards (close toward the user's eye), moving backwards (away from the user's eye), upwards, downwards, leftwards, rightwards, or moving circularly in a clockwise direction or a counter-clockwise direction. When the display module is a screen of a display, the display can show dynamic images. Besides, the lens assembly can project an object image leaving away from the user's eyes or moving close toward the user's eyes. As a result, the eye muscles are exercised by being released to clearly observe the object image leaving the user's eyes, or being tightened to clearly observe the object image moving close toward the user's eyes.

Compared with the prior arts, the present invention has advantages described below.

The display module is controlled by the control unit. The lens assembly can project an object image according to the light sources displayed by the display module. The object image appears to move close toward the user's eyes or leave away from the user's eyes, such that the user can exercise the eyes by releasing or tightening the ciliary muscles. In addition, the object image of the light spot can move upwards, downwards, leftwards, rightwards, or move circularly. The user can correspondingly roll the eyes upwards, downwards, leftwards, rightwards, or roll the eyes circularly to trace the object image for exercising the extraocular muscles. The eye muscles can be therefore thoroughly trained. Vision defects, such as myopia and astigmatism, can be relieved.

The display module and the lens assembly are mounted in the portable electronic device. The user can easily take the present invention by hands and use it anywhere and anytime.

BRIEF DESCRIPTION OF THE DRAWINGS

FIG. 9b is a plane view of the display module displaying a pattern different from the pattern of FIG. 9a;

DETAILED DESCRIPTION OF THE PREFERRED EMBODIMENT

Figure 1:
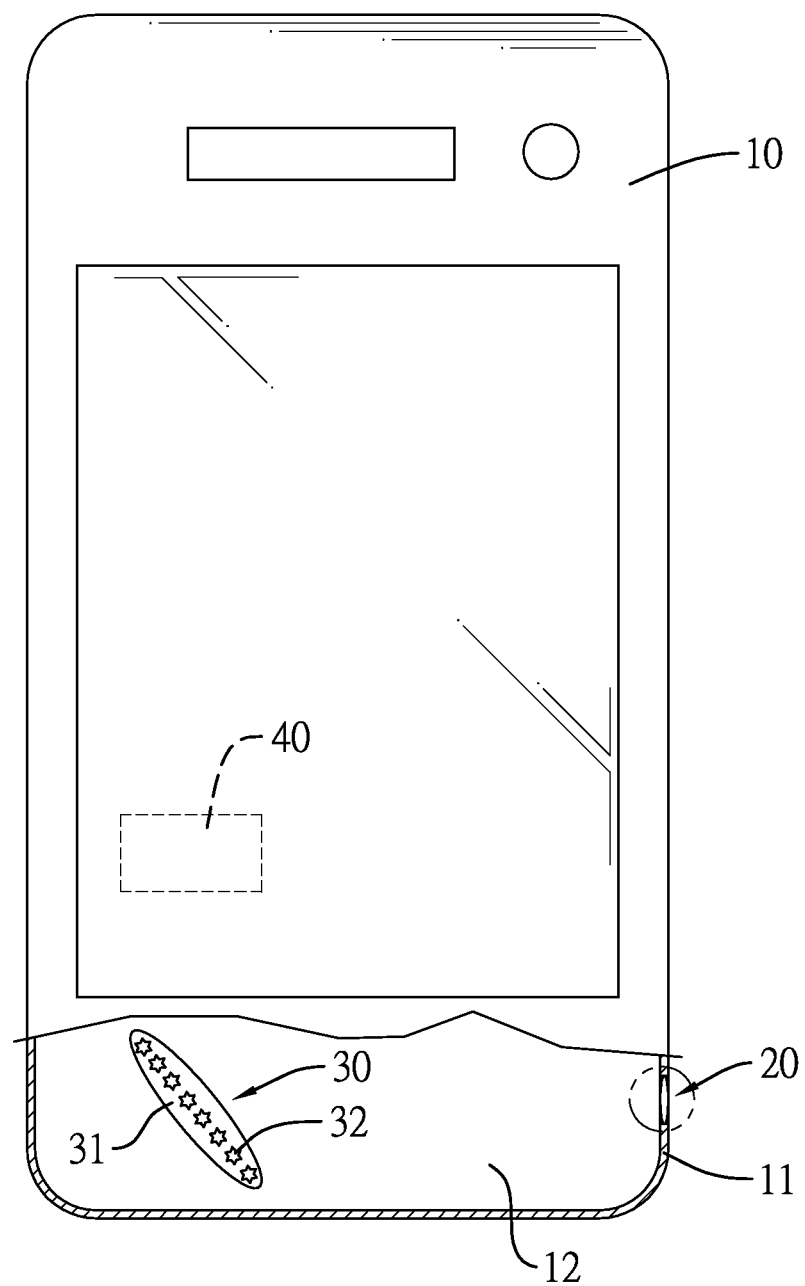
FIG. 1 is a partially sectional view of an embodiment of the portable electronic apparatus of the present invention.
Figure 2:
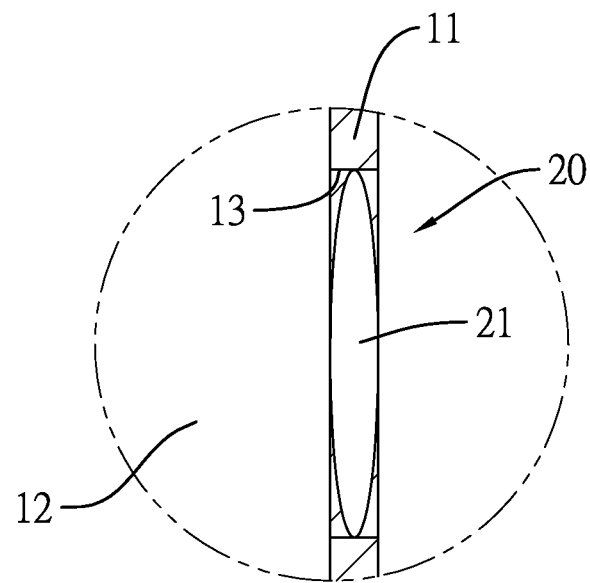
FIG. 2 is a partially enlarged view of the portable electronic apparatus in FIG. 1.
Figure 3:
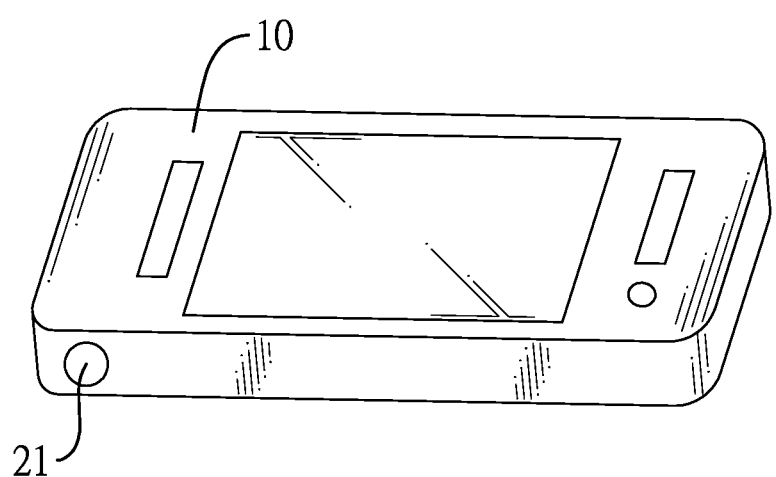
FIG. 3 is a perspective view of an embodiment of the portable electronic apparatus of the present invention.

With reference to FIGS. 1 to 3, a first embodiment of a portable electronic apparatus of the present invention has a portable electronic device 10, a lens assembly 20, a display module 30 and a control unit 40.

The portable electronic device 10 has a shell 11 with a chamber 12 and an opening 13. The chamber 12 is formed in the shell 11 and shielded by the shell 11 from exterior light. The opening 13 is formed on the shell 11 and communicates with the chamber 12. A length of the portable electronic device 10 is shorter than or equal to 40 centimeters. The portable electronic device 10 can be a smart phone, a notebook computer or a tablet.

The lens assembly 20 is mounted in the opening 13 of the shell 11. The lens assembly 20 can be a convex lens 21 or a combination of multiple lenses. A focal length of the lens assembly 20 can be smaller than 40 centimeters.

The display module 30 is mounted in the chamber 12 of the portable electronic device 10 and is at a position opposite to the lens assembly 20. The display module 30 can be mounted in parallel with the lens assembly 20, or can be mounted obliquely relative to the lens assembly 20. The display module 30 is electrically connected to and thus controlled by the control unit 40. The display module 30 can be a single light source 32, a group of light sources 32 mounted on a carrier 31, or a screen of a display. The light source 32 can be a light emitting diode (LED). The display module 30 is used to display a moving light spot or a series of patterns to form a dynamic image.

The control unit 40 is mounted in the portable electronic device 10, and is electrically connected to the display module 30 to activate the light sources 32 of the display module 30. For example, with reference to FIG. 1, the light sources 32 are LEDs. When the multiple light sources 32 are alternately and sequentially activated, the display module 30 displays a moving light spot. Alternatively, the control unit 40 can control the light sources 32 to show a series of patterns to form dynamic images.

Figure 4:
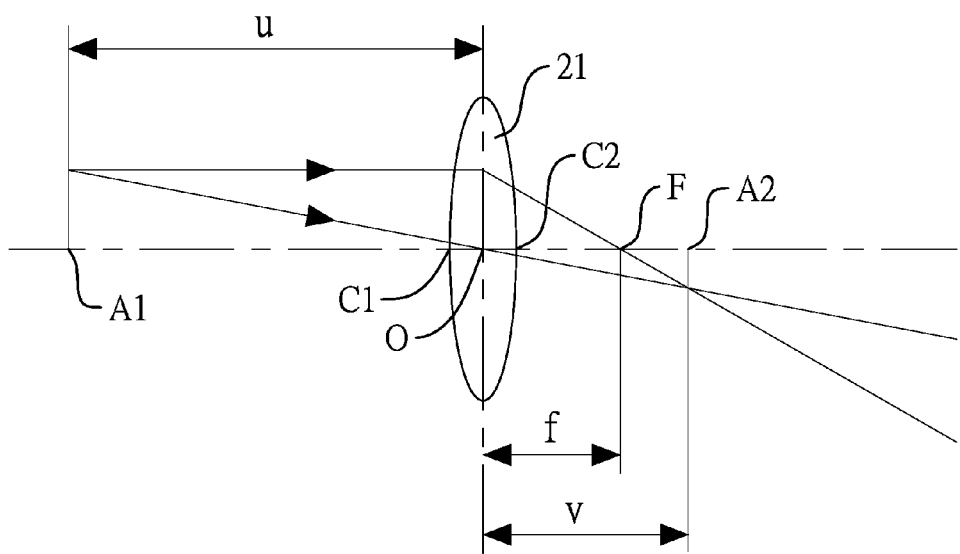
FIG. 4 is a schematic sketch showing a lens, a focal length (f), an image length (v) and an object length (u)

A common optical formula for a lens is defined as $$\frac{1}{u} + \frac{1}{v} = \frac{1}{f},$$

wherein u is an object length, v is an image length, and f is a focal length. According to the optical formula, the image length can be precisely defined by a user. With reference to FIG. 4, some optical nouns are briefly defined as below:

1. Principal axis or optic axis is a straight line that passes through C1 and C2, wherein C1 is a point located on a surface of the convex lens 21, and C2 is a point located on the other surface of the convex lens 21.

2. Optical center (O) is a point in the middle of the convex lens 21.

3. Focal point (F) is at a position where principal axis intersects a light refracted by the convex lens 21, wherein the light is in parallel with the principal axis before being refracted.

4. Focal length (f) is a distance between the focal point (F) and the optical center (O) of the convex lens 21.

5. Object length (u) is a distance between an object and the optical center (O) of the convex lens 21.

6. Image length (v) is a distance between an object image of the object and the optical center (O) of the convex lens 21.

7. A1 is a position where the object is located.

8. A2 is a position where the object image is formed.

Figure 5A:
FIG. 5a is a plane view of the display module displaying a light spot.

With reference to FIGS. 1 and 5a, a user can look at the convex lens 21 beside the portable electronic device 10. The object image can be projected to the user's eye, such that the user can see the object image. A position of A2 can be located in front of the user's eye, or approximates an infinite position. The display module 30 is controlled by the control unit 40. When the display module 30 is mounted in parallel with the lens assembly 20, the display module 30 can display a light spot moving forwards (close toward the user's eye), moving backwards (away from the user's eye), upwards, downwards, leftwards, rightwards or moving circularly. In another embodiment, when the display module 30 is mounted obliquely relative to the lens assembly 20, the display module 30 can display a light spot moving forwards (close toward the user's eye), moving backwards (away from the user's eye), moving upwards, moving downwards, moving leftwards, moving rightwards or moving circularly.

Embodiment 1-1

Figure 5B:
FIG. 5b is another plane view of the display module displaying a light spot.

With reference to FIG. 4, for example, the focal length (f) of the convex lens 21 is 0.4 centimeters. With reference to FIGS. 5a and 5b, the display module 30 is mounted obliquely from the lens assembly 20. Multiple LEDs as the light sources 32 are mounted on the carrier 31 along a virtual straight line. Each activated light source 32 as a light spot is illustrated in FIGS. 5a and 5b, the rest of the light sources 32 that are not activated are omitted. User's eyes 50 beside the lens assembly 20 can see the display module 30 through the lens assembly 20. When the light sources 32 are alternately activated, the display module 30 creates an object image of a moving light spot, such that the user can observe the object image of the moving light spot. When the object length (u) is 0.4 centimeters, the image length (v) approximates an infinite value. When the object length (u) is 0.3900 centimeters, the image length is 15.60 centimeters. The variations between the different object lengths (u) are small, and the scale of the image length (v) is relatively huge (from 15 centimeters to an infinite value). Hence, the object image of the activated light source 32 is like a far light spot or a near light spot observed by a person. TABLE 1 shows relationships of different focal lengths, the object lengths, and the image lengths of this embodiment.

TABLE 1

| Focal length (cm) | Object length (cm) | Image length (cm) |
|---|---|---|
| 0.4 | 0.3900 | −15.60 |
| 0.4 | 0.3999 | −1599.6 |
| 0.4 | 0.4000 | ∞ |

With reference to FIG. 4, the optical center (O) is regarded as a reference point. The object length (u) is positive in the case that the user's eye is at the right side of the convex lens 21 and the display module 30 is at the left side of the convex lens 21. The image length (v) is negative in the case that the display module 30 and the light spot displayed by the display module 30 are at the left side of the convex lens 21.

Embodiment 1-2

Based on the disclosure of the embodiment 1-1, the only difference between embodiments 1-2 and 1-1 is that the focal length (f) of the convex lens 21 in the embodiment 1-2 is 40 centimeters. When the object length (u) is 40 centimeters, the image length (v) approximates an infinite value. When the object length (u) is 11 centimeters, the image length (v) is 15.17 centimeters. Table 2 disclosed below shows relationships of different focal lengths, the object lengths, and the image lengths of this embodiment.

TABLE 2

| Focal length (cm) | Object length (cm) | Image length (cm) |
|---|---|---|
| 40 | 11.0 | −15.17 |
| 40 | 39.5 | −3160 |
| 40 | 40.0 | ∞ |

Embodiment 2-1

Figure 6A:
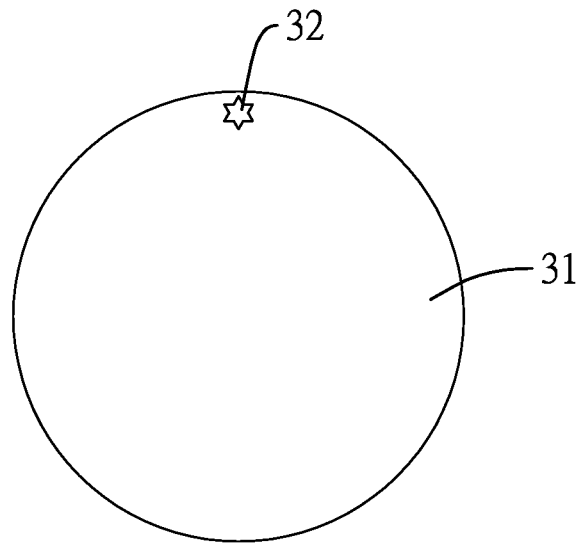
FIG. 6a is a plane view of the display module displaying a light spot on the top of the carrier.
Figure 6B:
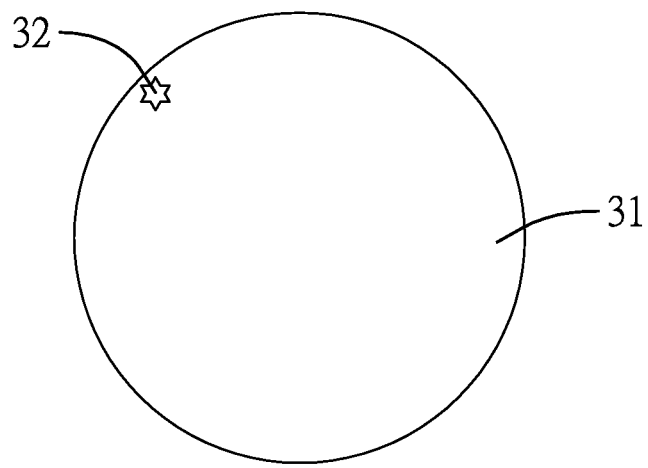
FIG. 6b is a plane view of the display module displaying a light spot on another point on the top of the carrier.

With reference to FIG. 4, for example, the focal length (f) of the convex lens 21 is 10 centimeters. The display module 30 is mounted in parallel with the lens assembly 20. With reference to FIGS. 6a and 6b, the carrier 31 of the display module 30 can be, but is not limited to, a circular panel. The multiple light sources 32 of the lens assembly 20 can be LEDs to form an LED array. Each activated light source 32 as a light spot is illustrated in FIGS. 6a and 6b, the rest of the light sources 32 that are not activated are omitted. When the object length (u) is 6.67 centimeters, the image length (v) is 20.03 centimeters. When the light sources 32 are alternately and sequentially activated in counterclockwise direction along an edge of the carrier 31, the user can observe an object image of the moving light spot created by the lens assembly 20. The eyes are rolled to trace the moving light spot to exercise the extraocular muscles of the eyes. Table 3 disclosed below shows relationships of different focal lengths, the object lengths, and the image lengths of this embodiment.

TABLE 3

| Focal length (cm) | Object length (cm) | Image length (cm) |
|---|---|---|
| 10 | 6.67 | −20.03 |
| 10 | 9.99 | −9990 |
| 10 | 10 | ∞ |

With reference to FIG. 4, the optical center (O) is regarded as a reference point. The object length (u) is positive in the case that the user's eye is at the right side of the convex lens 21 and the display module 30 is at the left side of the convex lens 21. The image length (v) is negative in the case that the display module 30 and the light spot displayed by the display module 30 are at the left side of the convex lens 21.

Embodiment 2-2

Figure 7A:
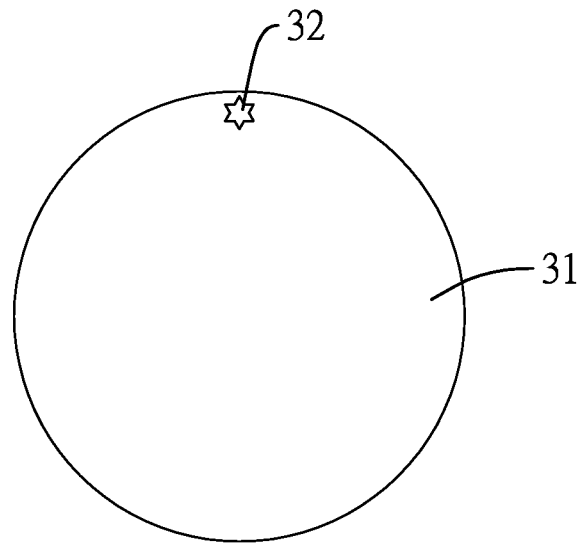
FIG. 7a is another plane view of the display module displaying a light spot on the top of the carrier.
Figure 7B:
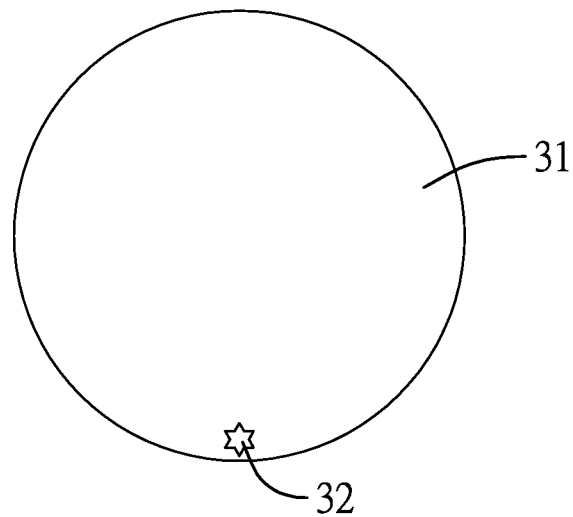
FIG. 7b is a plane view of the display module displaying a light spot on the bottom of the carrier.
Figure 8A:
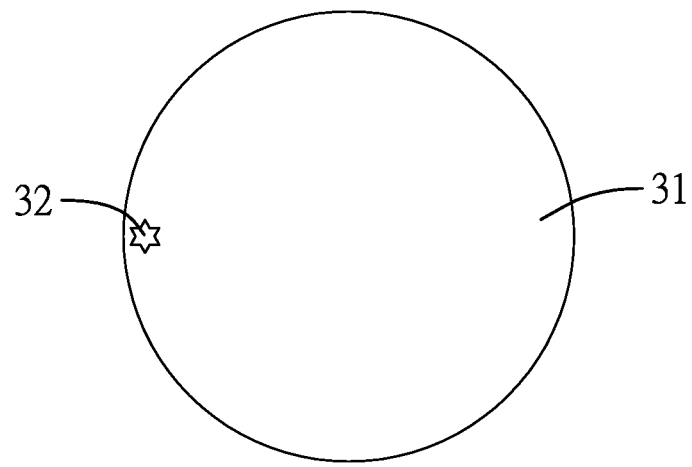
FIG. 8a is a plane view of the display module displaying a light spot on the left of the carrier.
Figure 8B:
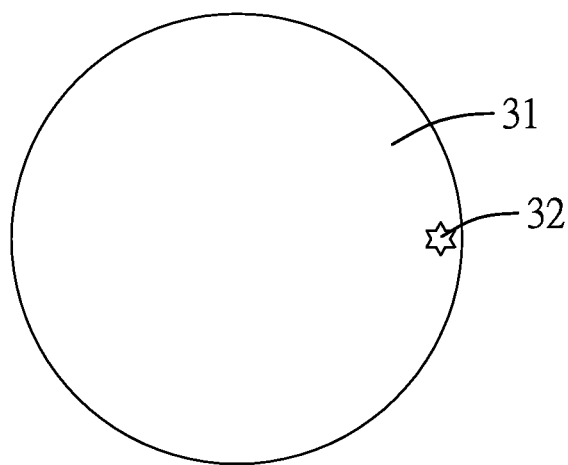
FIG. 8b is a plane view of the display module displaying a light spot on the right of the carrier.

Based on the embodiment 2-1, the difference between the embodiment 2-2 and the embodiment 2-1 is the movement of the light spot. With reference to FIGS. 7a and 7b, the light sources 32 on the top and the bottom of the carrier 31 are alternately activated for guiding the user's eye to trace the object image of the light spots, such that the user can roll the eyes upwards and downwards repeatedly. Similarly, with reference to FIGS. 8a and 8b, the light sources 32 on the left and the right of the carrier 31 are alternately activated, such that the user can roll the eyes leftwards and rightwards repeatedly for exercising the extraocular muscles of each eye.

Embodiment 3

Figure 9A:
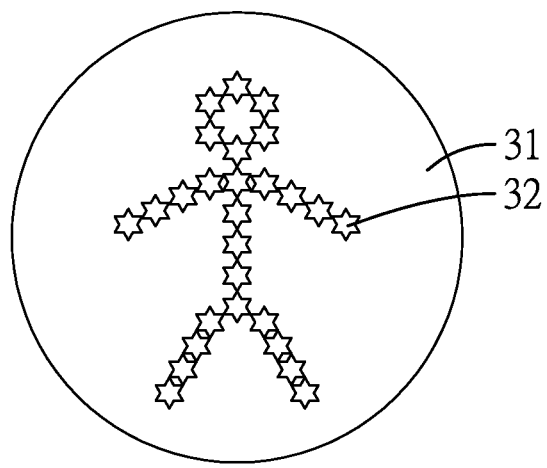
FIG. 9a is a plane view of the display module displaying a pattern.
Figure 9B:
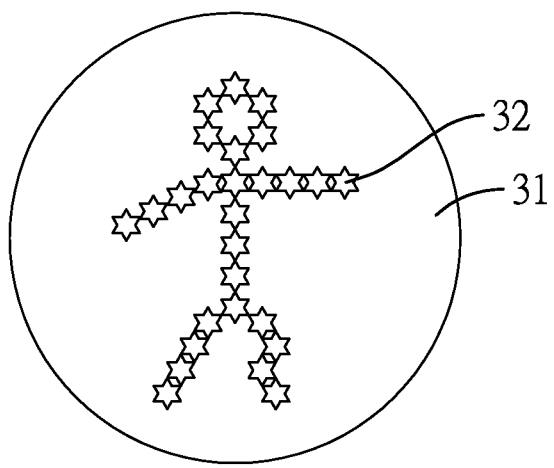

With reference to FIG. 4, for example, the focal length (f) of the convex lens 21 is 10 centimeters. The display module 30 is mounted in parallel to the lens assembly 20. The carrier 31 of the display module 30 can be, but is not limited to, a circular panel. The multiple light sources 32 can be LEDs and are mounted on the carrier 31 to form an LED array. Each activated light source 32 as a light spot is illustrated in FIGS. 9a and 9b, the rest of the light sources 32 that are not activated are omitted. The light spots can form different patterns. When the object length (u) is 9.99 centimeters, the image length (v) is 9990 centimeters according to TABLE 3. When the patterns in FIGS. 9a and 9b are alternately displayed by the display module 30, the patterns may form a dynamic object image, for example, a figure waving hands, to be projected into the user's eyes. The dynamic object image may attract the user's attention, such that the user is motivated to frequently use the present invention.

Embodiment 4

Figure 10A:
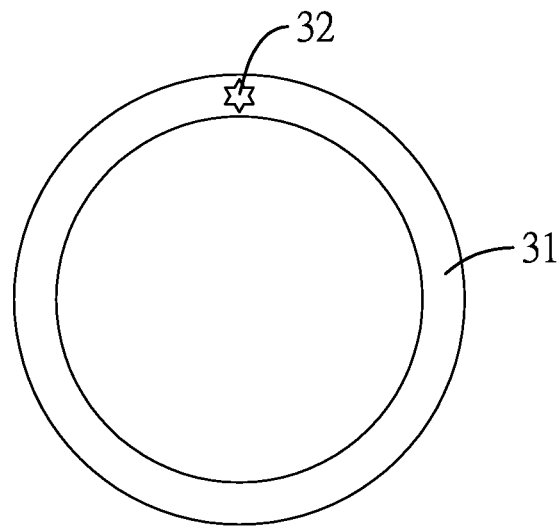
FIG. 10a is a plane view of the display module displaying a light spot on a ring-shaped carrier.
Figure 10B:
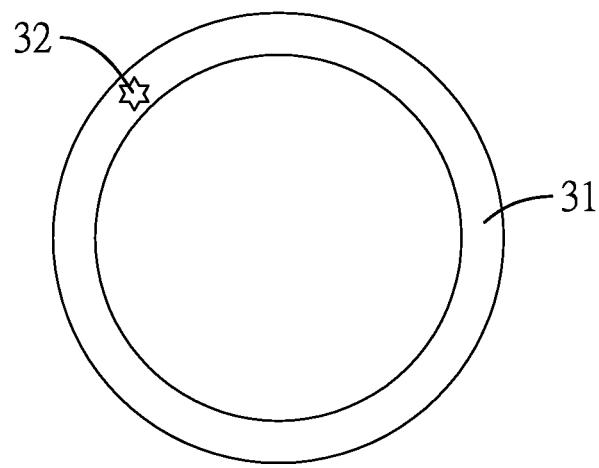
FIG. 10b is another plane view of the display module displaying a light spot on a ring-shaped carrier.

With reference to FIG. 4, for example, the focal length (f) of the convex lens 21 is 10 centimeters. The carrier 31 of the display module 30 can be a ring body, is mounted close to the portable electronic device 10, and is mounted in parallel to the lens assembly 20. The multiple light sources 32 are mounted on the carrier 31. Each activated light source 32 as a light spot is illustrated in FIGS. 10a and 10b, the rest of the light sources 32 that are not activated are omitted. When the object length (u) is 6.67 centimeters, the image length (v) is 20.03 centimeters according to TABLE 3. The light sources 32 are sequentially activated in counterclockwise direction for guiding the user's eye to trace the object image of light spots. As a result, the user can roll the eyes to trace the moving light spot for exercising the extraocular muscles of each eye.

Embodiment 5-1

Figure 11:
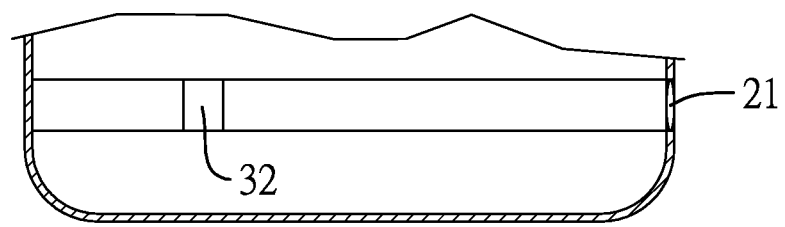
FIG. 11 is a partially sectional view of an embodiment of the portable electronic apparatus of the present invention.

With reference to FIG. 4, for example, the focal length (f) of the convex lens 21 is 10 centimeters. The display module 30 is mounted in parallel with the lens assembly 20. With reference to FIG. 11, the display module 30 is a single light source 32. When the object length (u) is 9.99 centimeters, the image length (v) is 9990 centimeters according to TABLE 3. The control unit 40 can activate the light source 32 for a while. When the light source 32 is activated, the display module 30 creates a far object image, such that the eyes observing the far object image can release the ciliary muscles. When the light source 32 is inactivated, the user's eye can take a break. By alternately activating and inactivating the light source 32, the ciliary muscles of the eyes are alternately released and tightened.

Embodiment 5-2

Figure 12:
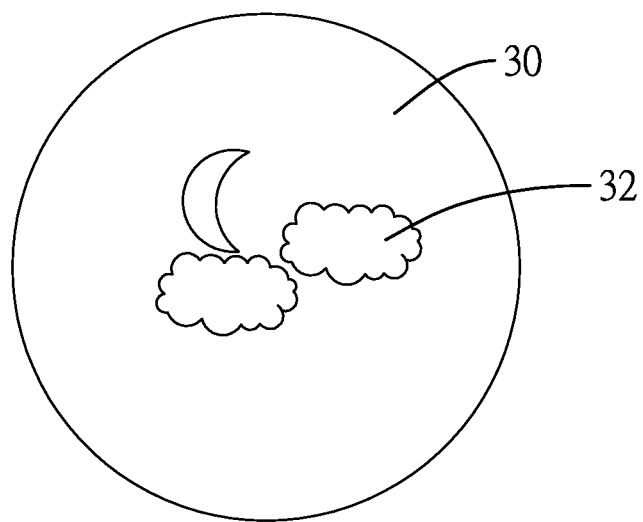
FIG. 12 is a plane view of the carrier as a screen of a display.

With reference to FIG. 4, for example, the focal length (f) of the convex lens 21 is 10 centimeters. The display module 30 is a screen of a display mounted in parallel to the lens assembly 20. With reference to FIG. 12, the light source 32 is a pattern displayed on the screen. When the object length (u) is 9.99 centimeters, the image length (v) is 9990 centimeters according to TABLE 3. When the light source 32 is activated, the display module 30 creates a far object image, such that the eyes observing the far object image can release the ciliary muscles. When the light source 32 is inactivated, the user's eye can take a break. By alternately activating and inactivating the light source 32, the ciliary muscles of the eyes are alternately released and tightened.

In the embodiments 1-1, 1-2, 2-1, 2-2, 3 and 4, the lens assembly 20 can create an object image based on at least one moving light spot displayed on a plane of the carrier 31, for guiding the user's eye to trace the moving light spot. In the embodiment 5-1, the display module 30 can be a single light source 32. In the embodiment 5-2, a screen of a display can form the display module 30.

In conclusion, according to the optical principle, the display module 30 and the lens assembly 20 can create an object image projecting into the user's eyes. The image length (v), the object length (u) and the focal length (f) can be precisely controlled, such that the user can observe an object image far from the user's eyes or an object image close to the user's eyes by using the portable electronic device 10 in a compact size, for exercising the eye muscles. The embodiments of the present invention disclose how the user roll the eyes upwards, downwards, leftwards, rightwards, or roll the eyes circularly by using the present invention, for exercising the extraocular muscles including the superior rectus muscle, the inferior rectus muscle, the medial rectus muscle, the lateral rectus muscle, the superior oblique muscle, and the inferior oblique muscle. The user exercises the eyes to decrease the risk of vision defects. Besides, the display module 30 can display different light spots or dynamic images to attract the user's attention and motivate the user to use the present invention. The user can therefore prevent the myopia and astigmatism for vision care.

What is claimed is:

1. A portable electronic apparatus having vision care functions, the portable electronic apparatus comprising:
    a portable electronic device being a smart phone and having a shell with a chamber and an opening communicating with the chamber, wherein the chamber is shielded from exterior light;
    a lens assembly mounted in the opening of the shell;
    a control unit mounted in the portable electronic device; and
    a display module mounted in the chamber of the portable electronic device at a position opposite to the lens assembly and controlled by the control unit, wherein the display module is covered by the shell of the portable electronic device, is unobservable from outside of the portable electronic device, and is selected from a single light source, a screen of a display, and a group of light sources.

2. The portable electronic apparatus as claimed in claim 1, wherein the lens assembly has at least one convex lens.

3. The portable electronic apparatus as claimed in claim 2, wherein a focal length of the lens assembly is smaller than 40 centimeters.

4. The portable electronic apparatus as claimed in claim 1, wherein the display module displays a dynamic image.

5. The portable electronic apparatus as claimed in claim 1, wherein the display module displays a light spot.

6. The portable electronic apparatus as claimed in claim 1, wherein the display module is mounted in parallel with the lens assembly.

7. The portable electronic apparatus as claimed in claim 1, wherein the display module is mounted obliquely relative to the lens assembly.

8. The portable electronic apparatus as claimed in claim 1, wherein the display module is only observable through the lens assembly.

* * * * *